(12) United States Patent
Ängeslevä

(10) Patent No.: US 6,464,647 B1
(45) Date of Patent: Oct. 15, 2002

(54) DEVICE AND METHOD FOR TESTING A NERVOUS SYSTEM

(76) Inventor: Cary Ängeslevä, Drabantvägen 17, Järfälla (SE), 117 50

(*) Notice: Subject to any disclaimer, the term of this patent is extended or adjusted under 35 U.S.C. 154(b) by 0 days.

(21) Appl. No.: 09/849,953

(22) Filed: May 4, 2001

(51) Int. Cl.[7] .................................................. A61B 5/05
(52) U.S. Cl. ...................................................... 600/554
(58) Field of Search ................................ 600/546, 554, 600/558, 559

(56) References Cited

U.S. PATENT DOCUMENTS

| | | | |
|---|---|---|---|
| 4,064,870 A | * 12/1977 | Dumitrescu et al. | ........ 600/554 |
| 4,166,452 A | 9/1979 | Generales, Jr. | |
| 4,315,502 A | 2/1982 | Gorges | |
| 5,374,193 A | 12/1994 | Trachtman | |

FOREIGN PATENT DOCUMENTS

| | | |
|---|---|---|
| DE | 4318336 | 6/1994 |
| SE | 514856 | 5/2001 |

* cited by examiner

*Primary Examiner*—Scott M. Getzow
(74) *Attorney, Agent, or Firm*—Hovey Williams LLP

(57) ABSTRACT

The invention concerns devices and methods for testing the nervous system of a person. The device includes a pulse generator (16) that delivers stimulation pulses (P1, P2, P3) to stimulation members (11, 12, 13). Furthermore, the device includes an adjustment member (18) for adjusting the time interval (T) between stimulation pulses (P1, P2, P3) and/or for adjusting the difference in strength (_A) between different stimulation pulses (P1, P2, P3). With the help of a device or a method according to the invention, a comparison is done between the experience of a test person of the stimulation and measured differences in time interval (T) and/or strength (_A) between the different stimulation pulses (P1, P2, P3).

18 Claims, 2 Drawing Sheets

DEVICE AND METHOD FOR TESTING A NERVOUS SYSTEM

BACKGROUND OF THE INVENTION AND PRIOR ART

The present invention concerns devices and methods for testing the nervous system of a person. With the nervous system is in this application meant both that which is included in the brain and that which is arranged in other parts of the body. Injuries in the nervous system of the body may result in that the response of a person to different stimuli is delayed or may even be absent. Certain injuries in the nervous system may be difficult to detect. The present invention concerns devices and methods for testing the nervous system of a person, wherein an indication of injuries in the nervous system may be obtained.

U.S. Pat. No. 4,315,502 describes a device for training relaxation. The device comprises members for delivering light and sound signals to a person who is being trained. Light and sound signals may be emitted simultaneously or alternating. Furthermore, the left and the right eye or ear, respectively, may be stimulated simultaneously or alternating. The document in question describes however mainly relaxation training and does not describe the testing of the nervous system of a person.

U.S. Pat. No. 4,166,452 describes an apparatus for testing the response of a person to stimuli. These stimuli may concern vision, hearing and tactile sense. The testing is primarily done by measuring the reaction time of the person who is being tested in response to different stimuli. The apparatus that is described in the document comprises relatively complicated circuit solutions.

DE-C-4 318 336 describes a method and a device for training the ability to distinguish visual, additive and tactile stimuli. The document describes a device with a pulse generator that delivers electrical impulses. Electrical impulses to two different stimulation members, for example one for the right and one for the left side, may be delivered with an adjustable time delay. By varying this time delay, a person may be trained in distinguishing impulses which are close to each other in time.

SUMMARY OF THE INVENTION

The purpose of the present invention is to achieve devices and methods for in an efficient and relatively simple manner testing the nervous system of a person.

The purpose of the invention is achieved by a device for testing the nervous system of a person, comprising:
  at least a first and a second stimulation member for application on or at the person, which stimulation members are arranged to stimulate at least one sense organ of the person,
  a pulse generator arranged to deliver stimulation pulses to at least said first and second stimulation members,
  an adjustment member in the nature of a time interval adjuster for adjusting the time interval at least between a stimulation pulse of the first stimulation member and a proximate stimulation pulse of the second stimulation member, wherein said time interval adjuster is arranged such that said time interval is substantially continuously adjustable from a negative to a positive value and such that said time interval is adjustable to a time interval where the person experiences said stimulation pulses from the first and the second stimulation members as being simultaneous,
  a supervising unit arranged to determine said time interval when adjustment with the time interval adjuster has been done to the time interval where the person experiences said stimulation pulses from the first and the second stimulation members as being simultaneous, and
  an output generator, for presenting said determined time interval to a user of the device.

With the help of the device, one or more sense organs may be stimulated with the help of stimulation members which are arranged at different parts of the body of the test person. Said time interval may then be adjusted until the test person experiences that the stimulation pulses from the first and the second stimulation members occur simultaneously. The supervising unit determines however if there still is a time interval between the delivered stimulation pulses. This time interval is presented to a user of the device. If there is a certain time interval between the stimulation pulses, in spite of the fact that the test person experiences these pulses as simultaneous, this may indicate the presence of injuries in the nervous system of the test person.

According to an embodiment of the invention, the device is arranged such that the stimulation pulses are delivered at a certain frequency f to said first and second stimulation members, wherein this frequency f is the same for the first and the second stimulation member. Since the stimulation pulses are delivered with a certain frequency, the test person has the possibility to sense many different stimulation pulses. With the help of the time interval adjuster, the difference in time may be continuously adjusted until the test person experiences the pulses from the first and the second stimulation members as being simultaneous. According to another embodiment of the invention, the device is arranged such that said time interval with the help of the time interval adjuster is adjustable up to a maximum absolute value $T_{max}$, wherein $T_{max} < 1/f$. This means that the time interval with the help of the time interval adjuster may not be adjusted so much that it is unclear which pulse of the first stimulation member that corresponds to another pulse of the second stimulation member. According to this embodiment, the risk of lack of clarity in the interpretation of the determined time interval is thus reduced.

According to another embodiment of the invention, said first and second stimulation members are arranged to stimulate different sense organs of the person. A comparison of the reaction of a test person on the stimulation of different sense organs may thus be performed. The sense organs which are used are primarily hearing, vision and tactile sense. Taste and smell should not be excluded, but since these senses do not occur so exactly at a certain moment in time, it is somewhat more difficult to make a comparison with these senses.

According to another embodiment of the invention, said first and second stimulation members are arranged to stimulate the same sense organ of the person. Thereby, for example the stimulation of vision may be carried out for the left and the right eye, or for different parts of the visual field of the same eye. A corresponding test is also possible for other sense organs, primarily for hearing and for the tactile sense.

According to a further embodiment of the invention, the device comprises a time interval evaluator arranged to evaluate whether said determined time interval falls within a, for said stimulation pulses of the first and the second stimulation members, predetermined interval. Such a predetermined interval may for example have been determined in advance and stored in a memory. This predetermined interval may for example constitute a normal difference in time interval at a stimulation of different parts of a body of a test person, which stimulation may be carried out for the same or for different sense organs. The device may thus be arranged to analyse whether the determined time interval is to be considered as normal or not.

The purpose of the invention is also achieved by a method for testing the nervous system of a person, comprising:

applying at least a first and a second stimulation member on or at the person who is to be tested, which stimulation members are arranged to stimulate at least one sense organ of the person, delivering stimulation pulses to at least said first and second stimulation members with the help of a pulse generator, adjusting the time interval at least between a stimulation pulse of the first stimulation member and a stimulation pulse of the second stimulation member with the help of a time interval adjuster until the person who is being tested experiences said stimulation pulses from the first and the second stimulation members as being simultaneous, determining said time interval when adjustment with the time interval adjuster been done until said time interval where the person experiences said stimulation pulses from the first and the second stimulation members as being simultaneous.

This method may for example be carried out with the above-mentioned device. By means of this method, the advantages described above in connection with device are thus achieved.

According to a preferred embodiment of the method, the adjustment of the time interval is done by the person who is being tested. The test person may thus adjust said time interval until the person experiences the stimulations as being simultaneous.

According to another preferred embodiment of the method, the stimulation pulses are delivered with a certain frequency f to said first and second stimulation members, wherein this frequency f is the same for the first and the second stimulation members. Thereby, the advantage described above, in connection with the device, is achieved.

According to another embodiment of the method according to the invention, said first and second stimulation members stimulate different sense organs of the person. According to a further embodiment of the method, said first and second stimulation members stimulate the same sense organ of the person. The method according to the invention thus comprises the possibilities which have been described above in connection with the device.

According to a further preferred embodiment, the method comprises evaluating whether said determined time interval falls within a, for said stimulation pulses of the first and the second stimulation members, predetermined interval. This evaluation may thus be used to determine whether the determined time interval is normal or not. If the determined time interval is not normal, the evaluation may comprise the determination of the fact that an injury may be the case in the nervous system.

The purpose of the invention is also achieved by a device for testing the nervous system of a person, comprising:

at least a first and a second stimulation member for application on or at the person, which stimulation members are arranged to stimulate at least one sense organ of the person, a pulse generator arranged to deliver stimulation pulses to at least said first and second stimulation members, an adjustment member for adjusting the difference in strength at least between a stimulation pulse of the first stimulation member and a stimulation pulse of the second stimulation member, wherein said strength difference adjuster is arranged such that said difference in strength is essentially continuously adjustable from a negative to a positive value and such that said difference in strength is adjustable to a difference where the person experiences said stimulation pulses from the first and the second stimulation members as having the same strength, a supervising unit arranged to determine said difference in strength when adjustment with the strength difference adjuster has been done to the difference in strength where the person experiences said stimulation pulses from the first and the second stimulation members as having the same strength, an output generator for presenting said determined difference in strength to a user of the device.

According to this embodiment, the strength of the stimulation pulses are thus adjusted instead of the time interval. It should be noted that a device according to the invention may be arranged to allow adjustment both of the strength and of the time interval. When using such a device it may thus be chosen whether the time interval or the strength is to be analysed.

According to an embodiment of this device, said first and second stimulation members are arranged to stimulate the same sense organ of the person. Since it may be difficult to compare the strength when different sense organs are stimulated, it is according to this embodiment preferred that the same sense organ is stimulated. It should however not be excluded that a comparison of the strength may be done also when stimulating different sense organs.

According to another embodiment of the device according to the invention, the device comprises a strength difference evaluator arranged to evaluate whether said determined difference in strength falls within a, for said stimulation pulses of the first and the second stimulation members, predetermined interval. Such an interval may for example indicate that which constitutes a normal difference in the experienced strength.

The purpose of the invention is also achieved by a method for testing the nervous system of a person, comprising:

applying at least a first and a second stimulation member on or at the person who is to be tested, which stimulation members are arranged to stimulate at least one sense organ of the person, delivering stimulation pulses to at least said first and second stimulation members with the help of a pulse generator, adjusting the difference in strength at least between a stimulation pulse of the first stimulation member and a stimulation pulse of the second stimulation member with the help of a strength difference adjuster until the person who is being tested experiences said stimulation pulses from the first and the second stimulation members as having the same strength, determining said difference in strength when adjustment with the adjustment means has been done to the difference in strength where the person experiences said stimulation pulses from the first and the second stimulation members as having the same strength.

According to this method of the invention, the advantages described above in connection with the device are achieved.

Further advantages of the present invention will be clear from the remaining dependent claims and from the following description.

SHORT DESCRIPTION OF THE DRAWINGS

The present invention will now be explained with the help of embodiments described as examples and with reference to the annexed drawings.

DETAILED DESCRIPTION OF EMBODIMENTS OF THE INVENTION

Figure 1:
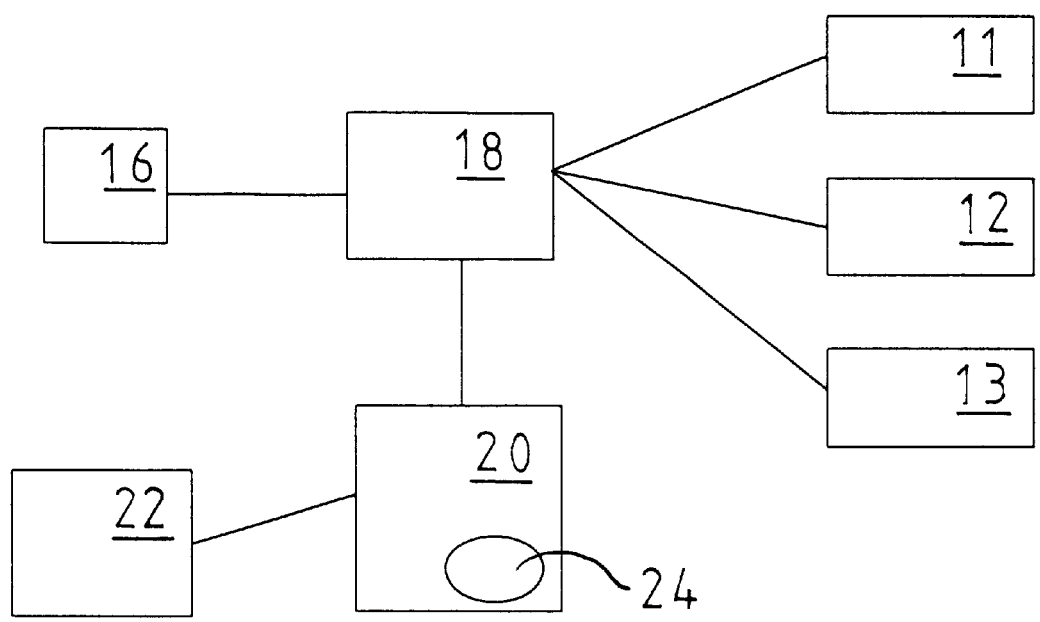
FIG. 1 shows schematically a block diagram of an embodiment of the invention.

FIG. 1 shows an embodiment of the device according to the invention. The device comprises a first 11, a second 12 and a third 13 stimulation member. According to the invention, the device comprises at least two stimulation members. In the shown embodiment, the device thus has three stimulation members. It is also possible to have more than three stimulation members. These stimulation members 11, 12, 13 are arranged to be able to be applied in association with a test person for stimulating at least one sense organ of the person, that is, on, at or sufficiently near to the person to be perceived by a sense organ. The sense organs involved are primarily hearing (ears), vision (eyes) and tactile sense (skin). Stimulation members for stimulating these senses are well known to the person skilled in the art and will therefore not be described more closely in this application. In, for example, the above cited documents, examples of such stimulation members are given. In order to stimulate the vision, for example bulbs or light emitting diodes may be used which are arranged in a mask intended to be arranged in front of the eyes. For stimulating the hearing, head phones may be used. For stimulating the tactile sense, electrical impulses may be applied with the help of electrodes attached to appropriate locations on the person's body.

When using the device, the stimulation members 11, 12, 13 may be constructed to stimulate the same or different sense organs of the person. The device may for example be arranged such that the stimulation members 11, 12, 13 are exchangeable.

The device comprises a pulse generator 16 which delivers stimulation pulses P1, P2, P3 to the stimulation members 11, 12, 13. The device may also comprise members (not shown) for changing the duration of a pulse and the shape of a pulse. The duration, the shape and the strength of a pulse must be such that the pulse is detected by the test person. Examples of such pulse generators include amplifier circuits and the like which create pulses provided to the stimulation members, such as strobing pulses to a light bulb or light emitting diode for visual stimulation, audio amplifiers which provide electrical pulses to loudspeakers or headphones, or electrical pulses to electrodes.

The device also comprises an adjustment member 18 such as a time interval adjuster. According to a first embodiment, the time interval T between a stimulation pulse P1, of a first stimulation member 11, and a proximate stimulation pulse P2 of a second stimulation member 12, may be adjusted with the help of this time interval adjuster 18. When the device comprises more than two stimulation members 11, 12, 13 which are used simultaneously, the time interval adjuster 18 is arranged such that the time interval between the pulses P1, P2, P3 of all stimulation members 11, 12, 13 may be adjusted. Said time interval T is with the help of the time interval adjuster 18 essentially continuously adjustable from a negative to a positive value. This means, for example, that it may be adjusted whether the pulse P1 shall occur before or after the pulse P2. The time interval T is adjustable to a time interval where a person who is being tested experiences said stimulation pulses P1, P2, P3 from the different stimulation members 11, 12, 13 as being simultaneous. This may for example mean that the adjustment means 18 shall be arranged such that said time interval T may be adjusted to have a value of between +500 ms and −500 ms, or between +1000 ms and −1000 ms.

Preferably, the device is arranged such that the stimulation pulses P1, P2, P3 are delivered with a certain frequency f to said stimulation members 11, 12, 13. This frequency f is thereby the same for the different stimulation members 11, 12, 13. Furthermore, it is preferably the case that the time interval T should not be adjustable to a higher absolute value than the formula $T_{max} < 1/f$ is fulfilled. This means for example that if the time interval T is adjustable up to +−1000 ms, then the frequency f should not be higher than 1 Hz, preferably the frequency f is essentially lower than this in order to avoid the confusion of the different stimulation pulses P1, P2, P3. The frequency f may thus for example be maximised to 0,5Hz, or 0,2Hz.

The device also comprises a supervising unit 20. This supervising unit 20 may for example constitute a computer which is operatively connected to the time interval adjuster 18, for example by a cable. The supervising unit 20 is arranged to determine said time interval T when adjustment with the time interval adjuster 18 has been done until the time interval T is such that the test person experiences said stimulation pulses P1, P2, P3 as being simultaneous. The device may for example be arranged such that the test person may press a button when the stimulation pulses P1, P2, P3 are experienced as being simultaneous. A signal may thereby be sent to the supervising unit.

Furthermore, the device comprises an output generator 22 for presenting said determined time interval T to a user of the device. The output generator 22 for presenting may for example constitute a computer screen, speaker or a printer. The user of the device may be a person who supervises the use of the device, for example a medical doctor.

The device may also comprise an evaluator 24 arranged to evaluate whether the determined time interval T falls within a predetermined interval. For example, it may thereby be determined whether the determined time interval T is normal for the stimulation that has been carried out. Said means for evaluating may form part of the supervising unit 20 and may thereby constitute a computer program stored in a memory and accessible to the computer.

It should be noted that the pulse generator 16 may be common to the different stimulation members 11, 12, 13. It is also possible to use different pulse generating means 16 for the different stimulation members 11, 12, 13. The adjustment member 18 may also comprise several adjustment controls (not shown) for the different stimulation members 11, 12, 13. The adjustment member 18 may for example constitute a joystick, mouse or keyboard. Such a joystick, mouse or keyboard may be used to set the time interval between the stimulation pulses P1, P2, P3 of two or three stimulation members 11, 12, 13. The adjustment member 18 in the form of a time interval adjuster may comprise one or more delay circuits (not shown) which delay the stimulation pulses P1, P2, P3 to the different stimulation members 11, 12, 13.

An example of a method according to the invention will now be described with reference to FIG. 1, 2 and 3.

Stimulation members 11, 12, 13 are applied to the person who is to be tested. As mentioned above, these stimulation members 11, 12, 13 may stimulate the same or different sense organs. For example, the stimulation member 11 may stimulate the tactile sense and for example constitute an electrode that is attached to for example a finger or another part of the body. The simulation member 12 may for example constitute a head phone that is applied to an ear for emitting signals for stimulating the hearing. The stimulation member 13 may for example constitute a light emitting diode that is arranged for stimulating an eye.

Figure 2:
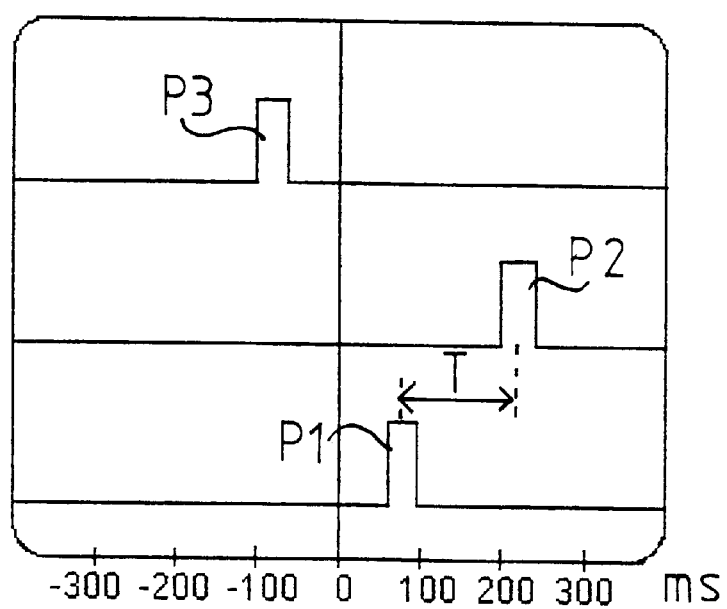
FIGS. 2, 3 show schematically the occurrence in time of different stimulation pulses.
Figure 3:
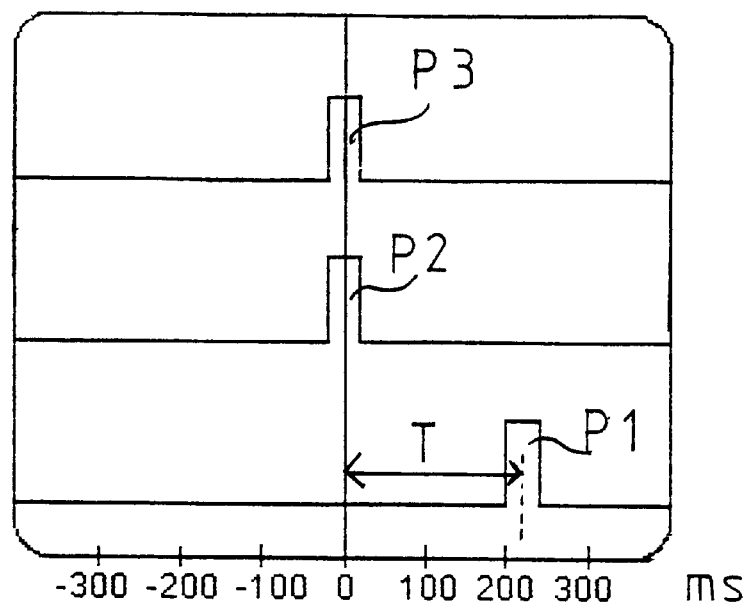

When the test begins, the stimulation pulses P1, P2, P3 may suitably occur at somewhat different moments in time such as shown in FIG. 2. Thereafter adjustment of the time intervals T between the different stimulation pulses P1, P2, P3 is done. In FIG. 2 only the time interval T between the stimulation pulses P1 and P2 is shown. The adjustment of the time interval T is preferably done by the test person. The adjustment of the time interval T is done until the test person experiences the stimulation pulses P1, P2, P3 as being simultaneous (if three stimulation members 11, 12, 13 are used, in fact three time intervals are adjusted: between the pulses P1 and P2, between P1 and P3 and between P2 and P3). An example of a performed adjustment is shown in FIG. 3. The method comprises thus the determination of said time interval T when the adjustment has been done with the help of the adjustment means 18 until the test person experiences the stimulation pulses P1, P2, P3 as being simultaneous. In the example shown in FIG. 3, the pulses P2 and P3 are simultaneous, which also the test person has experienced. However, the time interval T between the stimulation pulse P1 and the other stimulation pulses P2, P3 is larger than 0. In the shown example, this time interval T is about 220 ms. This means that the stimulation pulse P1 in reality was delivered 220 ms before the stimulation pulses P2 and P3 in spite of the fact that the test person experienced all stimulation pulses P1, P2, P3 as being simultaneous. The test person thus reacted later to the stimulation with the stimulation member 11 that emitted the stimulation pulse P1. This result is evaluated according to the method. In this evaluation it is decided whether said determined time interval T falls within a predetermined time interval for the performed stimulation. For example, this time interval may have been determined by a comparison of a larger population of normal test persons. It may thus for example be evaluated whether the test person in question has reacted normally on the stimulation. If the time interval T differs from what is normal, this may indicate an injury in the nervous system of the test person. For example, if the stimulation of the vision is experienced by the test person as being simultaneous with another stimulation in spite of the fact that the visual stimulation in reality took place at an earlier point in time than the other stimulation, this may indicate an injury in the visual nervous system of the test person.

According to an alternative embodiment of the device according to the invention, the device comprises the possibility of adjusting a difference in strength _A between different stimulation pulses P1, P2, P3, i.e. the adjustment member 18 is in this case a strength difference adjuster arranged to set a difference in strength _A between the different stimulation pulses P1, P2, P3 developed by the pulse generator 16 and delivered to the stimulation members. With strength is here primarily meant the amplitude of the stimulation pulses P1, P2, P3. The device according to the invention may of course be arranged to make it possible to adjust both the time interval and the strength. In other respects, the device of the embodiment for adjusting the strength corresponds to the device described above in connection with the adjustment of the time interval.

Figure 4:
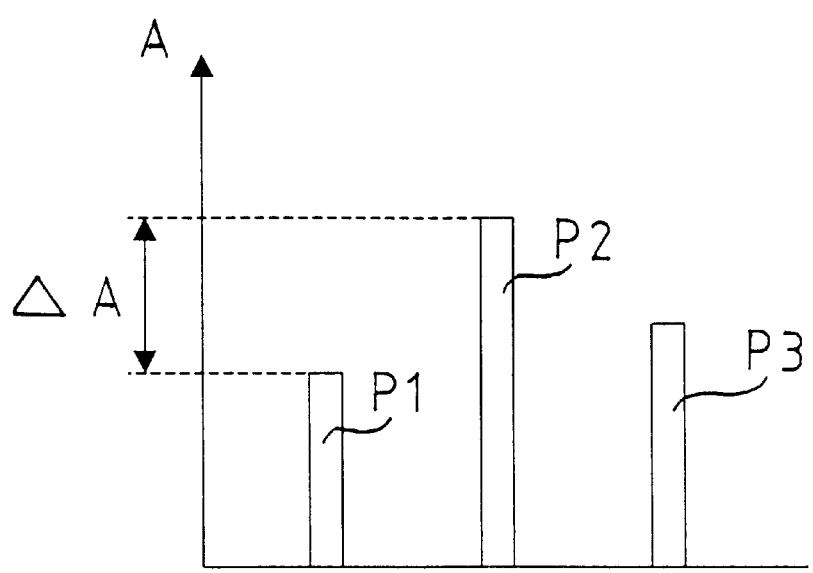
FIG. 4 shows schematically the difference in strength between different stimulation pulses.

FIG. 4 gives an example of a result when the test person has adjusted the difference in strength between three stimulation pulses P1, P2, P3 such that the test person experiences these stimulation pulses P1, P2, P3 as having the same strength. As can be seen in FIG. 4, the stimulation pulse P2 is in reality stronger than the stimulation pulse P1 and the stimulation pulse P3. Furthermore, the stimulation pulse P3 is stronger than the stimulation pulse P1. The difference in strength between the stimulation pulses P1 and P2 is in FIG. 4 marked with _A. The difference in strength between the different stimulation pulses P1, P2, P3 may for example be presented to a user on a screen in a similar manner as has been described above in connection with the adjustment of the time interval. An evaluation may then take place in order to decide whether this difference in strength _A is normal or not. The method according to this embodiment concerning the adjustment of the difference in strength _A thus corresponds to the above described method for setting the time interval.

It may be noted that when the difference in strength _A is adjusted, the different stimulation members 11, 12, 13 may suitably be arranged to stimulate the same sense organ of the person, since it may otherwise be difficult for a test person to compare the strength of the stimulation pulses P1, P2, P3. However, it is also possible to stimulate different sense organs. In the evaluation it may thereby be performed a comparison with how previously examined populations experience the strength of the stimulation of different sense organs in relation to each other. It should be noted that when the difference in strength _A is detected, the pulses P1, P2, P3 do not necessarily have to be particularly short. In principle the pulses P1, P2, P3 may in this case be very long and thus in principle be perceived as a long continuous signal by the test person. When the device is arranged to detect the time interval T, the pulses P1, P2, P3 are suitably shorter in order to be able to be clearly distinguished in time. Suitably, the pulses P1, P2, P3 can have a square shape, but also other shapes of pulses are possible. With the help of the invention, a test of the nervous system of a person may thus be carried out in order to find whether the nervous system functions normally or not. Whether the result of the test is normal or not may be determined by comparing with examined normal populations. A certain normal delay when the device is arranged to determine the time interval T between for example a tactile stimulation pulse and a stimulation of another part of the body or of another sense organ may thus be taken into consideration at the evaluation. Many different tests may of course be carried out with the help of the device and the method according to the invention. For example, tactile pulses to different body parts may be compared. Furthermore, different parts of the visual field may be compared, or the left and the right eye or the left and the right ear etc.

It should be noted that the expression "essentially continuously adjustable" as used in this document includes the possibility that the time interval is adjustable in small discrete steps. It should also be noted that the adjustment member may be arranged to be manually adjusted (for example by the person being tested), but may also be arranged to be automatically adjusted. The latter possibility may for example be carried out in that the time interval between a pulse to a first and second stimulation member is varied automatically between for example +0,5 s and −0,5 s. After each such pair of pulses, the person tested may state whether he/she experienced that the pulses were simultaneous or whether the pulse to the first stimulation member occurred before or after the pulse to the second stimulation member. The time interval between the two pulses may for example be randomly varied within the range $\_0{,}5$ s. When the test person states that the pulses occur simultaneously, the supervising unit may evaluate whether the statement of the test person corresponds to the actual occurrence in time of the test pulses. In an analogues manner, also in the embodiments where the pulses differ in strength, this difference may be automatically or randomly varied within a predetermined range.

The present invention is not limited to the described embodiments but may be varied and modified within the scope of the following claims.

What is claimed is:

1. A device for testing the nervous system of a person, comprising:

at least a first and a second stimulation member for application in association with the person, which stimulation members are arranged to stimulate at least one sense organ of the person;

a pulse generator arranged to deliver stimulation pulses (P1, P2) to at least said first and second stimulation members;

a time interval adjuster for adjusting a time interval (T) at least between a stimulation pulse (P1) of the first stimulation member and a proximate stimulation pulse (P2) of the second stimulation member, wherein said time interval adjuster is arranged such that said time interval (T) is substantially continuously adjustable from a negative to a positive value and such that said time interval (T) is adjustable to a time interval where the person experiences said stimulation pulses (P1, P2) from the first and the second stimulation members as being simultaneous;

a supervising unit arranged to determine said time interval (T) when adjustment with the time interval adjuster has been done to the time interval (T) where the person first experiences said stimulation pulses (P1, P2) from the first and the second stimulation members as being simultaneous; and an output generator for presenting said determined time interval (T) to a user of the device.

2. A device according to claim 1, arranged such that the stimulation pulses (P1, P2) are delivered with a certain frequency (f) to said first and second stimulation members, wherein this frequency (f) is the same for the first and the second stimulation members.

3. A device according to claim 2, arranged such that said time interval (T) with the help of the time interval adjuster is adjustable up to a maximum absolute value $|T|_{max}$, wherein $|T|_{max} < 1/f$.

4. A device according to claim 1, wherein said first and second stimulation members are arranged to stimulate different sense organs of the person.

5. A device according to claim 1, wherein said first and second stimulation members are arranged to stimulate the same sense organ of the person.

6. A device according to claim 1, further comprising an evaluator arranged to evaluate whether said determined time interval (T) falls within a predetermined interval for said stimulation pulses P1 and P2 of the first and the second stimulation members.

7. A method for testing the nervous system of a person, comprising:

applying at least a first and a second stimulation member in association with the person who is to be tested, which stimulation members are arranged to stimulate at least one sense organ of the person;

delivering stimulation pulses (P1,P2) to at least said first and second stimulation members with the help of a pulse generator;

adjusting the time interval (T) at least between a stimulation pulse (P1) of the first stimulation member and a stimulation pulse (P2) of the second stimulation member with the help of a time interval adjuster until the person who is being tested experiences said stimulation pulses (P1,P2) from the first and the second stimulation members as being simultaneous;

determining said time interval (T) when adjustment with the time interval adjuster has been done to said time interval where the person experiences said stimulation pulses (P1, P2) from the first and the second stimulation members as being simultaneous.

8. A method according to claim 7, wherein adjustment of the time interval (T) is done by the person being tested.

9. A method according to claim 7, wherein the stimulation pulses (P1, P2) are delivered with a certain frequency (f) to said first and second stimulation members, wherein this frequency (f) is the same for the first and the second stimulation members.

10. A method according to claim 7, wherein said first and second stimulation members stimulate different sense organs of the person.

11. A method according to claim 7, wherein said first and second stimulation members stimulate the same sense organ of the person.

12. A method according to claim 7, further comprising the step of evaluating whether said determined time interval (T) falls within a predetermined interval for said stimulation pulses (P1, P2) of the first and the second stimulation members.

13. A device for testing the nervous system of a person, comprising:

at least a first and a second stimulation member for application in association with the person, which stimulation members are arranged to stimulate at least one sense organ of the person;

a pulse generator arranged to deliver stimulation pulses (P1, P2) to at least said first and second stimulation members;

a strength difference adjuster for adjusting the difference in strength (AA) at least between a stimulation pulse (P1) of the first stimulation member and a stimulation pulse (P2) of the second stimulation member, wherein said strength difference adjuster is arranged such that said difference in strength ($\Delta A$) is essentially continuously adjustable from a negative to a positive value and such that said difference in strength ($\Delta A$) is adjustable to a difference where the person experiences said stimulation pulses (P1, P2) from the first and the second stimulation members as having the same strength;

a supervising unit arranged to determine said difference in strength ($\Delta A$) when adjustment with the strength difference adjuster has been done to the difference in strength ($\Delta A$) where the person experiences said stimulation pulses (P1, P2) from the first and the second stimulation members as having the same strength; and an output generator for presenting said determined difference in strength to a user of the device.

14. A device according to claim 13, wherein said first and second stimulation members are arranged to stimulate the same sense organ of the person.

15. A device according to claim 13, comprising an evaluator arranged to evaluate whether said determined difference in strength (ΔA) falls within a predetermined interval for said stimulation pulses (P1, P2) of the first and the second stimulation members.

16. A method for testing the nervous system of a person, comprising:

applying at least a first and a second stimulation member in association with the person who is to be tested, which stimulation members are arranged to stimulate at least one sense organ of the person;

delivering stimulation pulses (P1, P2) to at least said first and second stimulation members with the help of a pulse generator;

adjusting the difference in strength (ΔA) at least between a stimulation pulse (P1) of the first stimulation member and a stimulation pulse (P2) of the second stimulation member with the help of a strength difference adjuster until the person who is being tested experiences said stimulation pulses (P1, P2) from the first and the second stimulation members as having the same strength;

determining said difference in strength (ΔA) when adjustment with the strength difference adjuster has been done to the difference in strength (ΔA) where the person experiences said stimulation pulses (P1, P2) from the first and the second stimulation members as having the same strength.

17. A method according to claim 16, wherein said first and second stimulation members stimulate the same sense organ.

18. A method according to claim 16, further comprising the step of evaluating whether said determined difference in strength (ΔA) falls within a predetermined interval for said stimulation pulses (P1, P2) of the first and the second stimulation members.

* * * * *